United States Patent
Fatheree

(10) Patent No.: US 8,399,501 B2
(45) Date of Patent: *Mar. 19, 2013

(54) CRYSTALLINE ALKOXYIMIDAZOL-1-YLMETHYL BIPHENYL CARBOXYLIC ACID AND METHODS FOR PREPARING THEREOF

(75) Inventor: Paul R. Fatheree, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/039,573

(22) Filed: Mar. 3, 2011

(65) Prior Publication Data
US 2011/0218224 A1 Sep. 8, 2011

Related U.S. Application Data

(60) Provisional application No. 61/310,367, filed on Mar. 4, 2010.

(51) Int. Cl.
*A61K 31/417* (2006.01)
*C07D 233/64* (2006.01)
(52) U.S. Cl. ........... 514/398; 548/316.4; 548/326.5
(58) Field of Classification Search ............. 548/316.4, 548/326.5; 514/398
See application file for complete search history.

(56) References Cited

U.S. PATENT DOCUMENTS

| | | | |
|---|---|---|---|
| 7,855,221 B2 * | 12/2010 | Chao et al. | 514/398 |
| 7,879,896 B2 | 2/2011 | Allegretti et al. | |
| 2007/0082055 A1 | 4/2007 | Kurgan et al. | |
| 2008/0058399 A1 | 3/2008 | Abrahamsson et al. | |
| 2008/0269305 A1 * | 10/2008 | Allegretti et al. | 514/381 |
| 2010/0081697 A1 | 4/2010 | Chao et al. | |

FOREIGN PATENT DOCUMENTS

| | | |
|---|---|---|
| EP | 1 997 479 | 12/2008 |
| WO | WO 2005/123720 A1 | 12/2005 |

OTHER PUBLICATIONS

U.S. Appl. No. 12/891,964, Zhang et al.
PCT International Search Report for PCT/US2011/026958 dated Jun. 7, 2011.

* cited by examiner

*Primary Examiner* — Kamal Saeed
*Assistant Examiner* — Janet L Coppins
(74) *Attorney, Agent, or Firm* — Jeffrey A. Hagenah; Shelley Eberle

(57) ABSTRACT

The invention provides a micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid having improved stability. The invention also provides pharmaceutical compositions comprising the stable micronized compound, processes for preparing the stable micronized compound, and methods of using the stable micronized compound to treat diseases such as hypertension.

16 Claims, 1 Drawing Sheet

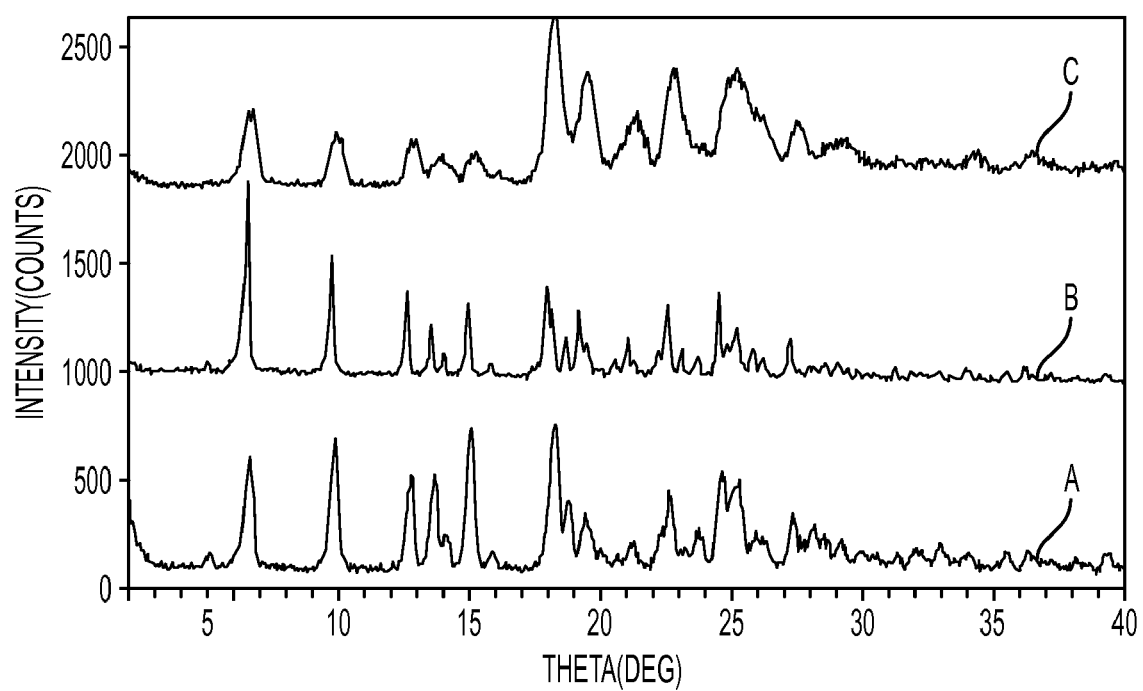

CRYSTALLINE ALKOXYIMIDAZOL-1-YLMETHYL BIPHENYL CARBOXYLIC ACID AND METHODS FOR PREPARING THEREOF

CROSS-REFERENCE TO RELATED APPLICATIONS

This application claims the benefit of U.S. Provisional Application No. 61/310,367, filed on Mar. 4, 2010; the entire disclosure of which is incorporated herein by reference.

BACKGROUND OF THE INVENTION

1. Field of the Invention

The present invention relates to a micronized alkoxyimidazol-1-ylmethyl biphenyl carboxylic acid crystalline compound having improved stability. This invention also relates to pharmaceutical compositions comprising the stable micronized compound, processes for preparing the stable micronized compound, and methods of using the stable micronized compound to treat diseases such as hypertension.

2. State of the Art

U.S. Publication Nos. 2008/0269305 and 2009/0023228, both to Allegretti et al. filed on Apr. 23, 2008, disclose novel compounds that possess $AT_1$ receptor antagonist activity and neprilysin (NEP) enzyme inhibition activity, the disclosures of which are incorporated herein by reference. In particular, the compound, 4'-{2-ethoxy-4-ethyl-5-[((S)-2-mercapto-4-methylpentanoylamino)methyl]imidazol-1-ylmethyl}-3'-fluorobiphenyl-2-carboxylic acid is described in these applications. The chemical structure of this compound is represented by formula I:

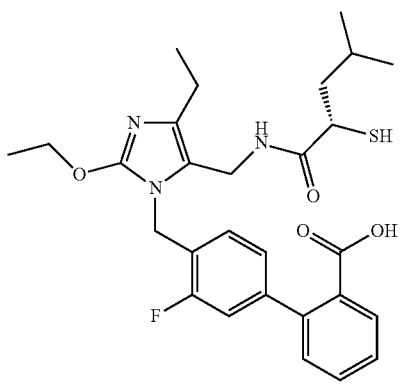

(I)

When preparing compounds for long term storage and when preparing pharmaceutical compositions and formulations, it is often desirable to have a crystalline form of the therapeutic agent that is neither hygroscopic nor deliquescent. It is also advantageous to have a crystalline form that has a relatively high melting point, which allows the material to be processed without significant decomposition. A crystalline freebase form of the compound of formula I is described in U.S. Publication No. 2010/0081697, to Chao et al. filed on Sep. 29, 2009, the disclosure of which is incorporated herein by reference.

Although this crystalline material has been found to be stable, it is desirable to further enhance the stability, in particular during mechanical processing such as milling or micronization, since particle size reduction of this crystalline material may have an adverse effect on its chemical stability. Attempts have been made to address chemical stability brought about by mechanical stress, in for example, U.S. Publication No. 2007/0082055 to Kurgan et al., where candesartan cilexetil was found to have improved stability when fine particles were slurried in an alcohol solvent. However, such techniques are often specific to particular crystalline forms.

Accordingly, there remains a need to obtain a stable micronized form of 4'-{2-ethoxy-4-ethyl-5-[((S)-2-mercapto-4-methylpentanoylamino)methyl]imidazol-1-ylmethyl}-3'-fluorobiphenyl-2-carboxylic acid.

SUMMARY OF THE INVENTION

The present invention relates to a crystalline freebase 4'-{2-ethoxy-4-ethyl-5-[((S)-2-mercapto-4-methylpentanoylamino)methyl]imidazol-1-ylmethyl}-3'-fluorobiphenyl-2-carboxylic acid having improved stability. In one embodiment, the invention relates to stable micronized 4'-{2-ethoxy-4-ethyl-5-[((S)-2-mercapto-4-methylpentanoylamino)-methyl]imidazol-1-ylmethyl}-3'-fluorobiphenyl-2-carboxylic acid (the "acid imidazole"), where the amount of 4'-{2-ethoxy-4-ethyl-5-[(2-mercapto-4-methylpentanoylamino)methyl]imidazol-1-ylmethyl}-3'-fluorobiphenyl-2-carboxylic acid ethyl ester (the "ethyl ester imidazole") within the stable micronized acid imidazole does not increase by more than about 0.1% AUC by HPLC relative to the initial amount of acid imidazole, when the stable micronized acid imidazole is maintained at a temperature of about 40° C. for at least 2 weeks. In one embodiment, the stable micronized acid imidazole is maintained in the presence of a desiccant such as molecular sieves.

Another embodiment of the invention encompasses a process for the preparation of the stable micronized acid imidazole, comprising a) micronizing a sample of 4'-{2-ethoxy-4-ethyl-5-[((S)-2-mercapto-4-methylpentanoylamino)methyl]imidazol-1-ylmethyl}-3'-fluorobiphenyl-2-carboxylic acid; b) forming a slurry with the sample and an inert diluent; c) recovering stable micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid, where the amount of 4'-{2-ethoxy-4-ethyl-5-[(2-mercapto-4-methylpentanoylamino)-methyl]imidazol-1-ylmethyl}-3'-fluorobiphenyl-2-carboxylic acid ethyl ester within the stable micronized acid imidazole does not increase by more than about 0.1% AUC by HPLC relative to the initial amount of acid imidazole, when the stable micronized acid imidazole is maintained at a temperature of about 40° C. for at least 2 weeks. Still another embodiment relates to the product of such process.

In another embodiment, the invention relates to stable micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid (the "acid imidazole"), where the amount of 4'-{4-ethyl-5-[(2-mercapto-4-methylpentanoylamino)methyl]-2-oxo-2,3-dihydroimidazol-1-ylmethyl}-3'-fluorobiphenyl-2-carboxylic acid (the "acid dihydroimidazole") within the stable micronized acid imidazole does not increase by more than about 0.1% AUC by HPLC relative to the initial amount of acid imidazole, when the stable micronized acid imidazole is maintained at a temperature of about 40° C. for at least 2 weeks. In one embodiment, the stable micronized acid imidazole is maintained in the presence of a desiccant such as molecular sieves.

Another embodiment of the invention encompasses a process for the preparation of the stable micronized acid, comprising a) micronizing a sample of 4'-{2-ethoxy-4-ethyl-5-[((S)-2-mercapto-4-methylpentanoylamino)methyl]imidazol-1-ylmethyl}-3'-fluorobiphenyl-2-carboxylic acid; b) forming a slurry with the sample and an inert diluent; c) recovering stable micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid, where the amount of 4'-{4-ethyl-5-[(2-mercapto-4-methylpentanoylamino)methyl]-2-oxo-2,3-dihydroimidazol-1-ylmethyl}-3'-fluorobiphenyl-2-carboxylic acid within the stable micronized acid imidazole does not increase by more than about 0.1% AUC by HPLC relative to the initial amount of acid imidazole, when the stable micronized acid imidazole is maintained at a temperature of about 40° C. for at least 2 weeks. Still another embodiment relates to the product of such process.

The stable micronized acid imidazole and the acid starting material are the same polymorph since both materials are characterized by a powder x-ray diffraction (PXRD) pattern comprising diffraction peaks at 2θ values of 6.66±0.20, 9.8±0.20, and 18.12±0.20; and further characterized by having one or more additional diffraction peaks at 2θ values selected from 12.68±0.20, 13.54±0.20, 15.02±0.20, 19.32±0.20, 21.20±0.20, 22.62±0.20, 24.56±0.20, 25.30±0.20, 25.96±0.20, and 27.32±0.20. The stable micronized acid imidazole of the invention may be further characterized by a DSC thermogram having an endotherm with a peak temperature of at least about 149° C.

The invention also encompasses pharmaceutical compositions comprising the stable micronized acid imidazole and a pharmaceutically acceptable carrier, and methods of treating hypertension or heart failure using the stable micronized acid imidazole.

BRIEF DESCRIPTION OF THE DRAWINGS

Various aspects of the present invention are illustrated by reference to the accompanying drawings.

FIG. 1 shows the powder x-ray diffraction (PXRD) patterns of the crystalline freebase of 4'-{2-ethoxy-4-ethyl-5-[((S)-2-mercapto-4-methylpentanoylamino)methyl]-imidazol-1-ylmethyl}-3'-fluorobiphenyl-2-carboxylic acid (A), the crystalline freebase of 4'-{2-ethoxy-4-ethyl-5-[((S)-2-mercapto-4-methylpentanoylamino)methyl]imidazol-1-ylmethyl}-3'-fluorobiphenyl-2-carboxylic acid that has been micronized (B), and the crystalline freebase of 4'-{2-ethoxy-4-ethyl-5-[((S)-2-mercapto-4-methylpentanoylamino)-methyl]-imidazol-1-ylmethyl}-3'-fluorobiphenyl-2-carboxylic acid that has been micronized and slurried (C).

DETAILED DESCRIPTION OF THE INVENTION

The present invention relates to a crystalline form 4'-{2-ethoxy-4-ethyl-5-[((S)-2-mercapto-4-methylpentanoylamino)methyl]imidazol-1-ylmethyl}-3'-fluorobiphenyl-2-carboxylic acid having improved stability. This crystalline form is not associated with any counterions and is referred to herein as a freebase crystalline form.

The active agent (i.e., the compound of formula I) contains one chiral center having the (S) configuration. However, it will be understood by those skilled in the art that minor amounts of the (R) stereoisomer may be present in the compositions of the invention unless otherwise indicated, provided that the utility of the composition as a whole is not eliminated by the presence of such an isomer. In addition, since the compound of formula I contains both a basic moiety (imidazole), and an acidic moiety (carboxylic acid), it may exist as a zwitterion. The compound of formula I has $AT_1$ receptor antagonist activity and NEP inhibition activity. The stable micronized acid imidazole of the invention is expected to have the same activity, and thus the same utility in treating diseases such as hypertension and heart failure. Therefore, among other uses, the stable micronized acid imidazole of the invention is useful for preparing pharmaceutical compositions for treating hypertension or heart failure.

DEFINITIONS

When describing the compounds, compositions, methods and processes of the invention, the following terms have the following meanings unless otherwise indicated. Additionally, as used herein, the singular forms "a," "an" and "the" include the corresponding plural forms unless the context of use clearly dictates otherwise. The terms "comprising", "including," and "having" are intended to be inclusive and mean that there may be additional elements other than the listed elements. All numbers expressing quantities of ingredients, properties such as molecular weight, reaction conditions, and so forth used herein are to be understood as being modified in all instances by the term "about," unless otherwise indicated. Accordingly, the numbers set forth herein are approximations that may vary depending upon the desired properties sought to be obtained by the present invention. At least, and not as an attempt to limit the application of the doctrine of equivalents to the scope of the claims, each number should at least be construed in light of the reported significant digits and by applying ordinary rounding techniques.

As used herein, the phrase "having the formula" or "having the structure" is not intended to be limiting and is used in the same way that the term "comprising" is commonly used.

The term "melting point" as used herein means the temperature at which the maximum endothermic heat flow is observed by differential scanning calorimetry, for the thermal transition that corresponds to the solid-to-liquid phase change.

The term "pharmaceutically acceptable" refers to a material that is not biologically or otherwise unacceptable when used in the invention. For example, the term "pharmaceutically acceptable carrier" refers to a material that can be incorporated into a composition and administered to a patient without causing unacceptable biological effects or interacting in an unacceptable with other components of the composition. Such pharmaceutically acceptable materials typically have met the required standards of toxicological and manufacturing testing, and include those materials identified as suitable inactive ingredients by the U.S. Food and Drug Administration.

The term "therapeutically effective amount" means an amount sufficient to effect treatment when administered to a patient in need thereof, i.e., the amount of drug needed to obtain the desired therapeutic effect. For example, a therapeutically effective amount for treating hypertension is an amount of compound needed to, for example, reduce, suppress, eliminate or prevent the symptoms of hypertension, or to treat the underlying cause of hypertension. In one embodiment, a therapeutically effective amount is that amount needed to reduce blood pressure or the amount of drug needed to maintain normal blood pressure. On the other hand, the term "effective amount" means an amount sufficient to obtain a desired result, which may not necessarily be a therapeutic result. For example, when studying a system comprising an $AT_1$ receptor, an "effective amount" may be the amount needed to antagonize the receptor.

The term "treating" or "treatment" as used herein means the treating or treatment of a disease or medical condition (such as hypertension) in a patient, such as a mammal (particularly a human) that includes: (a) preventing the disease or medical condition from occurring, that is, prophylactic treatment of a patient; (b) ameliorating the disease or medical condition such as by eliminating or causing regression of the disease or medical condition in a patient; (c) suppressing the disease or medical condition such as by slowing or arresting the development of the disease or medical condition in a patient; or (d) alleviating the symptoms of the disease or medical condition in a patient. For example, the term "treating hypertension" would include preventing hypertension from occurring, ameliorating hypertension, suppressing hypertension, and alleviating the symptoms of hypertension (for example, lowering blood pressure). The term "patient" is intended to include those mammals, such as humans, that are in need of treatment or disease prevention or that are presently being treated for disease prevention or treatment of a specific disease or medical condition. The term "patient" also includes test subjects in which compounds of the invention are being evaluated or test subjects being used in a assay, for example an animal model.

The process for preparing the stable micronized acid imidazole of the invention comprises the steps of: a) micronizing a sample of 4'-{2-ethoxy-4-ethyl-5-[((S)-2-mercapto-4-methylpentanoylamino)methyl]imidazol-1-ylmethyl}-3'-fluorobiphenyl-2-carboxylic acid; b) forming a slurry with the sample and an inert diluent for about 1 to about 10 hours; c) recovering stable micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid. Details of these steps are described below.

Crystallization

It will be appreciated that while specific process conditions (i.e. crystallization temperatures, times, mole ratios of reactants, solvents, pressures, etc.) are given, other process conditions can also be used unless otherwise stated. In some instances, reactions or crystallizations were conducted at room temperature (about 20-25° C.) and no actual temperature measurement was taken. It is understood that room temperature can be taken to mean a temperature within the range commonly associated with the ambient temperature in a laboratory environment, and will typically be in the range of about 25° C. to about 50° C. In other instances, reactions or crystallizations were conducted at room temperature and the temperature was actually measured and recorded.

Generally, the crystallizations are conducted in a suitable inert diluent or solvent system, examples of which include, but are not limited to, methanol, ethanol, isopropanol, isobutanol, ethyl acetate, acetonitrile, dichloromethane, methyl t-butyl ether, and the like, and mixtures thereof, optionally containing water. Upon completion of any of the foregoing crystallizations, the crystalline product can be isolated from the reaction mixture by any conventional means such as precipitation, concentration, centrifugation and the like.

The crystalline 4'-{2-ethoxy-4-ethyl-5-[((S)-2-mercapto-4-methylpentanoylamino)-methyl]imidazol-1-ylmethyl}-3'-fluorobiphenyl-2-carboxylic acid starting material employed in the invention can be readily prepared from commercially available starting materials and reagents using the procedures described in the Examples, or using the procedures described in the commonly-assigned U.S. applications described in the Background section of this application. The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio. In general, the crystalline starting material can be prepared by treating 4'-{2-ethoxy-4-ethyl-5-[((S)-2-mercapto-4-methylpentanoylamino)methyl]imidazol-1-ylmethyl}-3'-fluorobiphenyl-2-carboxylic acid with an inert diluent to complete dissolution. Suitable inert diluents include by way of illustration and not limitation, acetone, acetonitrile, ethyl acetate, methyl ethyl ketone, methanol, ethanol, isopropanol, water, and so forth. Other suitable inert diluents include by way of illustration and not limitation, combinations of inert diluents such as acetone with water, acetonitrile with water, and methanol and water. In one particular embodiment, the inert diluent is acetone, acetonitrile or a combination of acetone with water. Generally, dissolution is conducted at a temperature ranging from about 20° C. to about 50° C., in one embodiment at a temperature ranging from about 30-45° C., and in another embodiment at a temperature of about 15-25° C. The solution is then cooled to form the crystalline product. In one particular embodiment, the solution is cooled to about 20-30° C. such as 25° C., and in and in another embodiment to about 0-8° C. such as 4° C. After a suitable amount of time, crystals will be observed. In one embodiment, crystals are observed after a period of about 20-24 hours, and in another embodiment, observed after a period of about 4 hours. Once crystals are observed, the volume of the mother liquor can be reduced and the crystals isolated and dried.

Micronization

Micronization is a common method of reducing crystal size, and can be done by, for example, conventional jet mill micronizing, and will typically yield particles ranging from about 0.1 to about 10.0 µm, or from about 0.5 to about 5.0 µm. In one embodiment, the crystalline compound is micronized such that at least about 90% of the particles have a diameter of less than about 10 µm. Other methods of reducing particle size may also be used such as fine milling, chopping, crushing, grinding, milling, screening, trituration, pulverization, and so forth, as long as the desired particle size can be obtained.

Slurrying Process

The slurrying process involves forming a slurry of the micronized crystalline freebase starting material and a suitable inert diluent, i.e., forming a suspicion of the micronized crystalline freebase in the diluent. After a suitable amount of time, the crystalline freebase having improved stability is recovered.

Typically, a sample of the micronized crystalline freebase starting material will be slurried in a suitable inert diluent. The inert diluent can be an organic solvent such as acetone, acetonitrile, ethyl acetate, isopropyl acetate, methyl ethyl ketone, methanol, ethanol, isopropanol, methyl t-butyl ether, toluene, and so forth. The inert diluents can also be a combinations of an organic solvent and water, example of which include, acetone with water (e.g., 5, 10, 20 or 30 volume % acetone), acetonitrile with water (e.g., 10, 20 or 30 volume % acetonitrile), methanol and water (e.g., 5, 10, 20 or 30 volume % methanol), isopropanol and water (e.g., 5, 10, 20 or 30 volume % isopropanol).

In one embodiment, the inert diluent is a combination of acetone with water. In one particular embodiment the volume ratio of acetone to water is about 5:95 to 40:60; in another embodiment about 10:90 to 30:70; and in yet another embodiment about 20:80.

Generally, slurrying is conducted at a temperature ranging from about 0° C. to about 50° C. In one embodiment, slurrying is conducted at about 0° C.; in another embodiment at slurrying is conducted at about room temperature; and in yet another embodiment, slurrying is conducted at about 40° C.

Typically, the slurrying step will be conducted for a suitable amount of time, which may range from about 1 to about 30 hours, and includes from about 1 to about 20 hours, about 1 to about 20 hours, about 1 to about 10 hours, and about 1 to about 5 hours. In one embodiment, slurrying is conducted for about 1 hour, 1.5 hours, 4 hours, or 5 hours; and in another embodiment, for about 2 to about 3 hours.

Once the slurrying step is completed, the slurrying diluent can be reduced and the improved crystalline freebase can be isolated and dried. This may involve steps such as cooling the sample, filtering the solids, evaporating the diluent, washing the solids, drying (for example, under nitrogen), and so forth. In one embodiment, after slurrying for a suitable amount of time, the solids are filtered then washed with the same or similar inert diluent used in the slurrying step. For example, the slurrying step may use a 20% acetone/water solution, and the solids may later be washed with a 10% acetone/water solution.

Compound Properties

As is well known in the field of powder x-ray diffraction, relative peak heights of PXRD spectra are dependent on a number of factors relating to sample preparation and instrument geometry, while peak positions are relatively insensitive to experimental details. A PXRD pattern was obtained as set forth in Example 4. Thus, in one embodiment, the stable micronized compound of the invention is characterized by a PXRD pattern having certain peak positions.

The crystalline compound (Example 1) is characterized by a PXRD pattern in which the peak positions are substantially in accordance with those shown in FIG. 1A. The micronized crystalline compound (Example 2) is characterized by a PXRD pattern in which the peak positions are substantially in accordance with those shown in FIG. 1B. The slurried micronized crystalline compound (Example 3; the stable micronized compound of the invention) is characterized by a PXRD pattern in which the peak positions are substantially in accordance with those shown in FIG. 1C. The three PXRD patterns are substantially the same and the peaks are listed below, in order of descending relative intensity.

| I % | 2-Theta |
|---|---|
| 100 | 18.121 |
| 76 | 6.658 |
| 64 | 9.801 |
| 62 | 22.621 |
| 52 | 19.324 |
| 51 | 24.561 |
| 44 | 12.682 |
| 40 | 15.019 |
| 37 | 25.296 |

-continued

| I % | 2-Theta |
|---|---|
| 30 | 27.318 |
| 27 | 13.543 |
| 27 | 21.199 |
| 19 | 25.958 |

A differential scanning calorimetry (DSC) trace was obtained as set forth in Example 5. Thus, in one embodiment, the stable micronized compound of the invention is characterized by its DSC thermograph. In one embodiment, the stable micronized compound of the invention is characterized by a DSC thermograph which shows a melting point of about 149° C.

The improved stability of the compound of the invention (referred to as the "acid imidazole") is determined by the amount of impurity present over time, as compared to the original amount of impurity present. For example, after storage at a temperature of about 40° C. for at least 2 weeks (with a desiccant such as molecular sieves), analysis of the stable micronized compound of the invention by high performance liquid chromatography (HPLC) showed minimal chemical degradation.

One impurity that may be present is 4'-{2-ethoxy-4-ethyl-5-[(2-mercapto-4-methylpentanoylamino)methyl]imidazol-1-ylmethyl}-3'-fluorobiphenyl-2-carboxylic acid ethyl ester (referred to as "M+28" or the "ethyl ester imidazole"), which is represented by the formula:

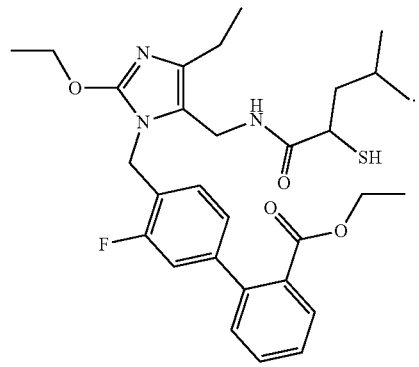

Thus, in one embodiment of the invention, "stable" is intended to mean the micronized acid imidazole, where the amount of the ethyl ester imidazole within the stable micronized acid imidazole does not increase by more than about 0.1% AUC by HPLC relative to the initial amount of acid imidazole, when the stable micronized acid imidazole is maintained at a temperature of about 40° C. for at least 2 weeks. In one embodiment, the micronized acid imidazole is maintained at a temperature of about 40° C. for at least 4 weeks.

Another impurity that may be present is 4'-{4-ethyl-5-[(2-mercapto-4-methylpentanoylamino)methyl]-2-oxo-2,3-dihydro-imidazol-1-ylmethyl}-3'-fluorobiphenyl-2-carboxylic acid (referred to as "M−28" or the "acid dihydroimidazole"), which is represented by the formula:

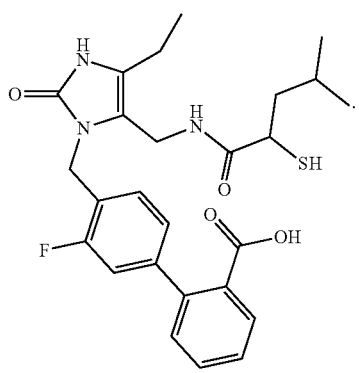

Thus, in another embodiment of the invention, "stable" is intended to mean the micronized acid imidazole, where the amount of the acid dihydroimidazole within the stable micronized acid imidazole does not increase by more than about 0.1% AUC by HPLC relative to the initial amount of acid imidazole, when the stable micronized acid imidazole is maintained at a temperature of about 40° C. for at least 2 weeks.

These properties of the stable micronized compound of the invention are further illustrated in the Examples below.

Pharmaceutical Compositions and Formulations

The stable micronized compound of the invention is typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal), ocular, and parenteral modes of administration. Further, the compound of the invention may be administered, for example orally, in multiple doses per day (for example, two, three, or four times daily), in a single daily dose or a single weekly dose. It will be understood by those skilled in the art that, once a crystalline compound has been formulated, it may no longer be in crystalline form, i.e., the crystalline compound may be dissolved in a suitable carrier.

Accordingly, in one embodiment, the invention relates to a pharmaceutical composition comprising a pharmaceutically acceptable carrier and stable micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid. Such pharmaceutical compositions may also contain other therapeutic and/or formulating agents if desired. When discussing compositions, the stable micronized compound of the invention may also be referred to herein as the "active agent" to distinguish it from other components of the formulation, such as the carrier.

The pharmaceutical compositions of the invention typically contain a therapeutically effective amount of the compound of the invention. Those skilled in the art will recognize, however, that a pharmaceutical composition may contain more than a therapeutically effective amount, such as in bulk compositions, or less than a therapeutically effective amount, that is, individual unit doses designed for multiple administration to achieve a therapeutically effective amount. Typically, the composition will contain from about 0.01-95 wt % of active agent, including, from about 0.01-30 wt %, such as from about 0.01-10 wt %, with the actual amount depending upon the formulation itself, the route of administration, the frequency of dosing, and so forth. In one embodiment, a composition suitable for an oral dosage form, for example, may contain about 5-70 wt %, or from about 10-60 wt % of active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable composition for a particular mode of administration is well within the scope of those skilled in the pharmaceutical arts. Additionally, carriers or excipients used in such compositions are commercially available. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; compressed propellant gases, such as chlorofluorocarbons and hydrofluorocarbons; and other non-toxic compatible substances employed in pharmaceutical compositions.

Pharmaceutical compositions are typically prepared by thoroughly and intimately mixing or blending the active agent with a pharmaceutically acceptable carrier and one or more optional ingredients. The resulting uniformly blended mixture may then be shaped or loaded into tablets, capsules, pills, canisters, cartridges, dispensers and the like using conventional procedures and equipment.

Since the compound of the invention contains a thiol group, additional consideration may be given to minimize or eliminate oxidation of the thiol to form a disulfide. In solid formulations, this may be accomplished by reducing the drying time, decreasing the moisture content of the formulation, and including materials such as ascorbic acid, ethylenediaminetetraacetic acid, sodium ascorbate, sodium sulfite and sodium bisulfate, as well as materials such as a mixture of lactose and microcrystalline cellulose. In liquid formulations, stability of the thiol may be improved by the addition of amino acids, antioxidants, or a combination of disodium edetate and ascorbic acid.

If desired, the compound of the invention may be administered in combination with one or more other therapeutic agents. Thus, in one embodiment, pharmaceutical compositions of the invention contain other drugs that are co-administered with the compound of the invention. For example, the composition may further comprise one or more therapeutic agents (also referred to as "secondary agents(s)") selected from the group of diuretics, $\beta_1$ adrenergic receptor blockers, calcium channel blockers, angiotensin-converting enzyme inhibitors, $AT_1$ receptor antagonists, neprilysin inhibitors, non-steroidal anti-inflammatory agents, prostaglandins, anti-lipid agents, anti-diabetic agents, anti-thrombotic agents, renin inhibitors, endothelin receptor antagonists, endothelin converting enzyme inhibitors, aldosterone antagonists, angiotensin-converting enzyme/neprilysin inhibitors, and combinations thereof. Accordingly, in yet another embodiment of the invention, a pharmaceutical composition comprises a compound of the invention, a second active agent, and a pharmaceutically acceptable carrier. Third, fourth etc. active agents may also be included in the composition. The compound of the invention may be physically mixed with the second active agent to form a composition containing both agents, or each agent may be present in separate and distinct compositions which are administered to the patient simultaneously or at separate times.

Secondary agent(s), when included, are present in a therapeutically effective amount such that they are typically administered in an amount that produces a therapeutically beneficial effect when co-administered with the compound of the invention. Suitable doses for these secondary agents administered in combination with the compound of the invention are in the range of about 0.05 μg/day to about 100 mg/day. The secondary agent can be in the form of a pharmaceutically acceptable salt, solvate, optically pure stereoisomer, prodrug, and so forth.

The amount of the compound of the invention administered per dose or the total amount administered per day may be predetermined or it may be determined on an individual patient basis by taking into consideration numerous factors, including the nature and severity of the patient's condition, the condition being treated, the age, weight, and general health of the patient, the tolerance of the patient to the active agent, the route of administration, pharmacological considerations such as the activity, efficacy, pharmacokinetics and toxicology profiles of the compound and any secondary agents being administered, and the like. Treatment of a patient suffering from a disease or medical condition (such as hypertension) can begin with a predetermined dosage or a dosage determined by the treating physician, and will continue for a period of time necessary to prevent, ameliorate, suppress, or alleviate the symptoms of the disease or medical condition. Patients undergoing such treatment will typically be monitored on a routine basis to determine the effectiveness of therapy. For example, in treating hypertension, blood pressure measurements may be used to determine the effectiveness of treatment. Similar indicators for other diseases and conditions described herein, are well known and are readily available to the treating physician. Continuous monitoring by the physician will insure that the optimal amount of the compound of the invention will be administered at any given time, as well as facilitating the determination of the duration of treatment. This is of particular value when secondary agents are also being administered, as their selection, dosage, and duration of therapy may also require adjustment. In this way, the treatment regimen and dosing schedule can be adjusted over the course of therapy so that the lowest amount of active agent that exhibits the desired effectiveness is administered and, further, that administration is continued only so long as is necessary to successfully treat the disease or medical condition.

EXAMPLES

The following Preparations and Examples are provided to illustrate specific embodiments of this invention. These specific embodiments, however, are not intended to limit the scope of this invention in any way unless specifically indicated.

The following abbreviations have the following meanings unless otherwise indicated and any other abbreviations used herein and not defined have their standard generally accepted meaning:

AcOH acetic acid $Bu_4NBr$ tetrabutylammonium bromide

DCC 1,3-dicyclohexylcarbodiimide

DCM dichloromethane or methylene chloride

DIPEA N,N-diisopropylethylamine

DMAP 4-dimethylaminopyridine

DMF N,N-dimethylformamide

DMSO dimethyl sulfoxide

DTT 1,4-dithiothreitol

EtOAc ethyl acetate

EtOH ethanol

HCTU (2-(6-chloro-1H-benzotriazole-1-yl)-1,1,3,3-tetramethylaminium hexafluorophosphate)

IPA isopropyl alcohol iPrOAc isopropyl acetate

MeCN acetonitrile

MeOH methanol

MTBE methyl t-butyl ether

NaOMe sodium methoxide

NBS N-bromosuccinimide

TFA trifluoroacetic acid

THF tetrahydrofuran

Unless noted otherwise, all materials, such as reagents, starting materials and solvents, were purchased from commercial suppliers (such as Sigma-Aldrich, Fluka Riedel-de Haën, Strem Chemicals, Inc., and the like) and were used without further purification.

Reactions were run under nitrogen atmosphere, unless noted otherwise. The progress of reactions were monitored by thin layer chromatography (TLC), analytical high performance liquid chromatography (anal. HPLC), and mass spectrometry, the details of which are given in specific examples. Solvents used in analytical HPLC were as follows: solvent A was 98% water/2% MeCN/1.0 mL/L TFA; solvent B was 90% MeCN/10% water/1.0 mL/L TFA.

Reactions were worked up as described specifically in each preparation or example; commonly reaction mixtures were purified by extraction and other purification methods such as temperature-, and solvent-dependent crystallization, and precipitation. In addition, reaction mixtures were routinely purified by preparative HPLC, typically using Microsorb C18 and Microsorb BDS column packings and conventional eluents. Characterization of reaction products was routinely carried out by mass and $^1$H-NMR spectrometry. For NMR measurement, samples were dissolved in deuterated solvent ($CD_3OD$, $CDCl_3$, or DMSO-$d_6$), and $^1$H-NMR spectra were acquired with a Varian Gemini 2000 instrument (400 MHz) under standard observation conditions. Mass spectrometric identification of compounds was typically conducted using an electrospray ionization method (ESMS) with an Applied Biosystems (Foster City, Calif.) model API 150 EX instrument or an Agilent (Palo Alto, Calif.) model 1200 LC/MSD instrument.

Preparation 1

5-Bromo-2-ethoxy-3H-imidazole-4-carbaldehyde

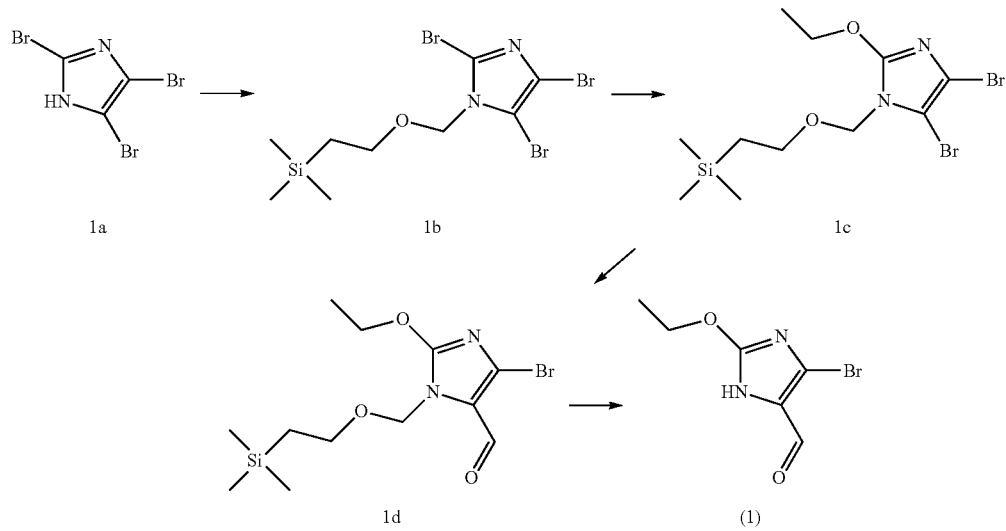 [SMILES: Brc1nc(Br)c(Br)[nH]1 ; C[Si](C)(C)CCOCn1c(Br)nc(Br)c1Br ; CCOc1nc(Br)c(Br)n1COCC[Si](C)(C)C ; CCOc1nc(Br)c(C=O)n1COCC[Si](C)(C)C ; CCOc1nc(Br)c(C=O)[nH]1]

2,4,5-Tribromo-1H-imidazole (1a) (98.7 g, 324 mmol, 1.0 eq) was dissolved into 1.20 L of DCM and cooled to 0° C. To this was added DIPEA (62 mL, 360 mmol, 1.1 eq) followed by the slow addition of [β-(trimethylsilyl)ethoxy]methyl chloride (60.2 mL, 340 mmol, 1.05 eq). The solution was slowly warmed to room temperature. After 2 hours the mixture was washed with 1M $H_3PO_4$/saturated aqueous NaCl (1:10; 2×600 mL). The organic layer was dried over $MgSO_4$, and evaporated to dryness, yielding intermediate (1b) as faint yellow liquid that solidified on standing (137 g).

Intermediate (1b) (130 g, 290 mmol, 1.0 eq) was dissolved into anhydrous EtOH (650 mL). To this was slowly added potassium t-butoxide (98.6 g, 879 mmol, 3.0 eq) and the mixture was heated to reflux for 16 hours. The mixture was then cooled to room temperature, filtered and concentrated. The resulting oil was dissolved in EtOAc (800 mL) and washed with saturated $NaHCO_3$ (400 mL). The layers were separated and the organic was washed with saturated aqueous NaCl, dried over $MgSO_4$, filtered and concentrated, yielding intermediate (1c) as a brown oil (115.3 g). MS m/z: [M+H$^+$] calcd for $C_{11}H_{20}Br_2N_2O_2Si$, 401.9 found 401.2.

Intermediate (1c) (69.5 g, 174 mmol, 1.0 eq) was dissolved in anhydrous THF (600 mL) and cooled to −78° C. under nitrogen. A 2.5M solution of n-butyllithium in hexanes (72.9 mL, 180 mmol, 1.05 eq) was added dropwise and the mixture was stirred at −78° C. for 10 minutes. DMF (40 mL, 520 mmol, 3.0 eq) was then added and the mixture was stirred at −78° C. for 15 minutes and was then warmed to room temperature. The reaction was quenched with water (10 mL), diluted with EtOAc (600 mL) and was washed with water (100 mL), saturated aqueous NaCl, dried over $MgSO_4$ and concentrated under reduced pressure. The recovered material was purified by silica gel chromatography (15-30% EtOAc: hexanes) to produce intermediate (1d) as a pale yellow oil (45 g).

Intermediate (1d) (105.8 g, 303 mmol, 1.0 eq) was cooled at 0° C. in ice. TFA (300 mL) was added and the mixture was stirred at 0° C. for 15 minutes, then warmed to room temperature. After 90 minutes the mixture was concentrated under reduced pressure and redissolved in EtOAc (700 mL). The organic was washed with saturated bicarbonate (2×600 mL), saturated aqueous NaCl, dried over $MgSO_4$, and concentrated under reduced pressure to produce a yellow solid. The material was suspended in hexanes (300 mL) and stirred at 0° C. for 30 minutes. The material was filtered and the solid was washed with cold hexanes (150 mL) to yield the title compound (1) as a pale white solid (61.2 g). $^1$H-NMR (CDCl$_3$) δ (ppm): 1.4 (m, 3H), 4.5 (m, 2H), 5.2 (s, 1H), 9.2 (d, 1H).

Preparation 2

4'-Bromomethyl-3'-fluorobiphenyl-2-carboxylic Acid t-Butyl Ester

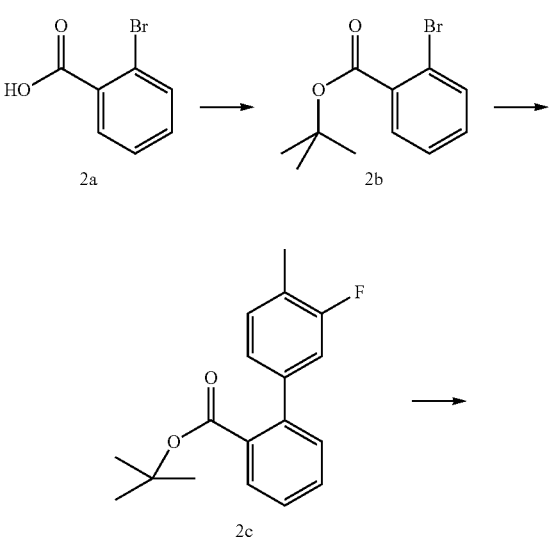

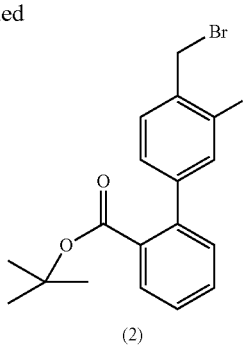

To a solution of 1.0M DCC in DCM (800 mL, 800 mol) cooled at 0° C. was added 2-bromobenzoic acid (2a) (161 g, 800 mmol) followed by DMAP (9.0 g, 740 mmol) and t-butyl alcohol (82.4 mL, 880 mmol). The mixture was stirred at room temperature for 10 minutes, then warmed to room temperature and stirred. After 16 hours, the mixture was then filtered. The organic was washed with saturated NaHCO$_3$ (400 mL), saturated aqueous NaCl, dried over MgSO$_4$, filtered and concentrated under reduced pressure to produce the crude intermediate (2b) as an oil (228.8 g).

The crude intermediate (2b) (109.6 g, 426 mmol) and 3-fluoro-4-methylphenyl-boronicacid (72.2 g, 449 mmol) were suspended in isopropyl alcohol (360 mL, 4.7 mmol). A 2.0M solution of sodium carbonate in water (360 mL, 720 mmol) was added and the mixture was degassed under nitrogen. Tetrakis(triphenylphosphine)palladium(0) (4.9 g, 4.3 mmol) was then added and the mixture was stirred at 90° C. for 46 hours. The mixture was cooled to room temperature, diluted with EtOAc (800 mL), and the layers were separated. The organic was washed with saturated aqueous NaCl and concentrated under reduced pressure. The recovered oil was purified by silica gel chromatography (3×4-6% EtOAc:hexanes) to yield intermediate (2c) as a clear oil (93.3 g).

Intermediate (2c) (89.8 g, 314 mmol, 1.0 eq) was dissolved in CCl$_4$ (620 mL, 6.4 mol) and was degassed under nitrogen. NBS (55.8 g, 314 mmol) was added, followed by benzoyl peroxide (1.5 g, 6.3 mmol) and the mixture was heated at 90° C. under nitrogen for 7 hours. The reaction was cooled in an ice bath, filtered, and concentrated under reduced pressure. The recovered oil was triturated with 150 mL of 3% EtOAc: hexanes. The solution was chilled at −20° C. for 2 hours, then filtered and washed with cold 3% EtOAc:hexanes solution (200 mL) to yield the title compound (2) as an off white solid (88.9 g). $^1$H-NMR (CDCl$_3$) δ (ppm): 1.3 (m, 9H), 4.6 (s, 2H), 7.0-7.1 (m, 2H), 7.3 (dd, 1H), 7.4 (m, 1H), 7.5 (m, 1H), 7.8 (dd, 1H).

Preparation 3

Crystalline 4'-(5-Aminomethyl-2-ethoxy-4-ethylimidazol-1-ylmethyl)-3'-fluorobiphenyl-2-carboxylic Acid t-Butyl Ester

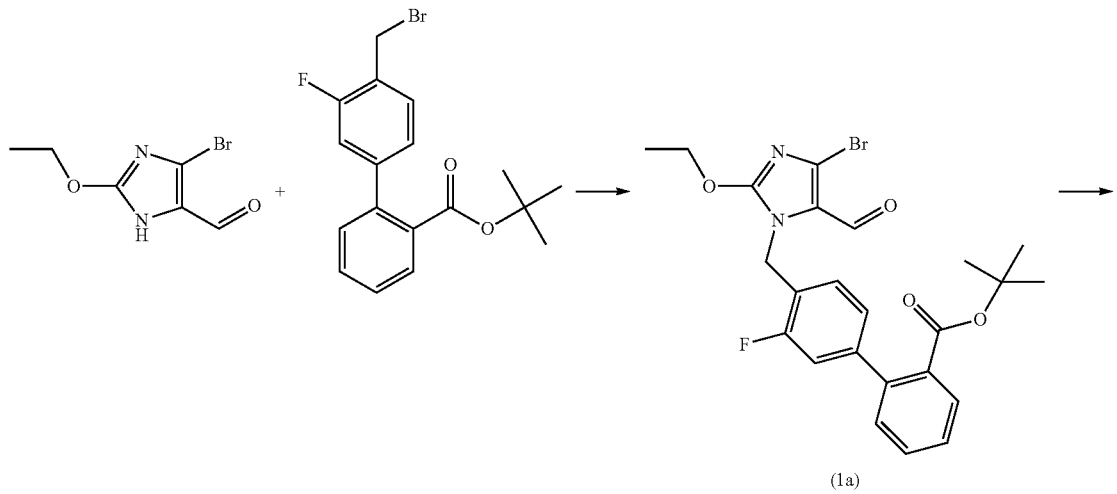

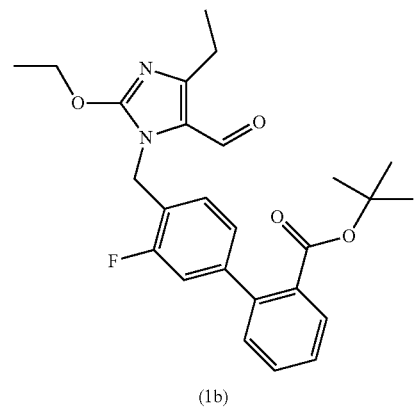

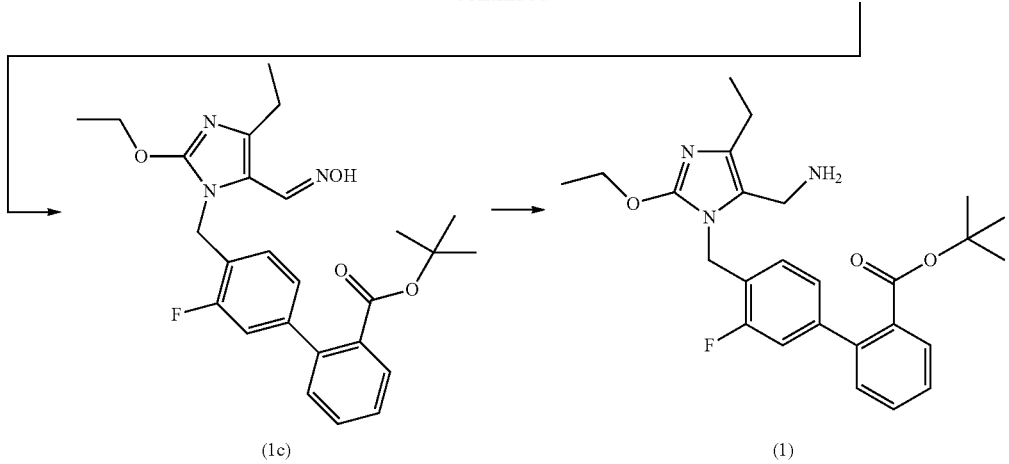

(1c) (1)

5-Bromo-2-ethoxy-3H-imidazole-4-carbaldehyde (22.0 g, 100 mmol, 1.1 eq.), 4'-bromomethyl-3'-fluorobiphenyl-2-carboxylic acid t-butyl ester (33.0 g, 90 mmol, 1 eq.), and Bu$_4$NBr (1.6 g, 5 mmol, 0.05 eq.) were dissolved in toluene (400 mL) and 1N NaOH (120 mL, 120 mmol, 1.2 eq.). The resulting mixture was stirred at 27° C. for 48-60 hours. The toluene layer was separated, washed with water (2×200 mL), then removed by distillation. EtOH (350 mL) was added to the residue and the mixture was heated to 50-60° C. until the solids dissolved. The mixture was cooled to room temperature over 4 hours, then cooled to 4° C. and stirred at 4° C. for 4 hours. The solids were filtered off, washed with cold EtOH (60 mL) and dried at room temperature under vacuum for 24 hours to yield intermediate (1a) (~39 g).

Intermediate (1a) (20.0 g, 40 mmol, 1 eq.), potassium ethyl trifluoroborate (7.1 g, 52 mmol, 1.3 eq.), palladium(II) acetate (224 mg, 1 mmol, 0.025 eq.), cataCXium® A (butyldi-1-adamantylphosphine; CAS#321921-71-5; 538 mg, 1.45 mmol, 0.04 eq.), and Cs$_2$CO$_3$ (45 g, 138 mmol, 3.45 eq.) were dissolved in toluene (240 mL) and water (80 mL). The mixture was flushed with nitrogen (3×) under vacuum, then heated to 90° C. for 16 hours. The mixture was then cooled to room temperature and the layers were separated. The organic layer was washed with water (2×200 mL) then distilled under reduced pressure to yield an oil. The oil was dissolved in EtOH (240 mL). Water (80 mL) was added and the mixture was stirred for 30 minutes. The mixture was filtered to remove solids, the solids were washed with 75% EtOH (130 mL), and the filtrate collected to yield intermediate (1b) in an EtOH solution, which was used directly in the next step.

The EtOH solution of intermediate (1b) (10 mmol, 1 eq.) was combined with hydroxylamine hydrochloride (27.2 g, 52 mmol, 1.3 eq.) and NaHCO$_3$ (35.2 g, 3.45 eq.). The mixture was stirred at 40° C. for 24 hours, then cooled to room temperature. The precipitant was filtered off, washed with 75% EtOH (100 mL) and 50% EtOH (200 mL), then dried under reduced pressure at 30° C. for 24 hours to yield intermediate (1c) (15 g).

Intermediate (1c) (5 g) was combined with EtOH (100 mL), NH$_4$OH (28%, 6 mL), and Raney nickel (wet 10 g) to form a slurry. The mixture was degassed under nitrogen (3×), degassed under hydrogen (3×), then stirred under hydrogen (1 atm) for 3 hours. The mixture was filtered to remove the catalyst and the solids were washed with EtOH (20 mL). The filtrate was then treated with charcoal (0.5 g) and filtered again. The filtrate was then distilled under vacuum to yield an oil. Heptanes were added (50 mL) and the mixture distilled to an oil (2×). The remaining oil was dissolved in heptanes (60 mL) by heating the mixture and stirring at 4° C. for 24 hours. The solids were then filtered, washed with cold heptanes (10 mL), and dried at room temperature for 24 hours to yield the title compound as a crystalline material (3.8 g).

Preparation 4

(S)-2-Acetylsulfanyl-4-methylpentanoic Acid

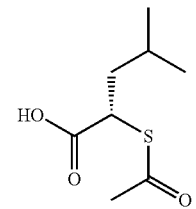

D-Leucine (8.2 g, 62.7 mmol) was dissolved in 3.0M HBr in water (99 mL, 0.3 mol) and cooled to 0° C. A solution of NaNO$_2$ (6.9 g, 100 mmol) in water (11.3 mL, 627 mmol) was slowly added over 20 minutes. The mixture was stirred at 0° C. for 3 hours and then extracted twice with ethyl ether, washed with water then saturated aqueous NaCl, dried over MgSO$_4$, filtered, and concentrated to afford (R)-2-bromo-4-methylpentanoic acid (11.5 g) as an off-yellow oil. This was taken on to the next step without further purification.

Thioacetic acid (4.2 g, 54.4 mmol) and DMF (100 mL, 1.0 mol) were combined, and the mixture cooled in an ice bath. Sodium carbonate (5.8 g, 54.4 mmol) was added. After 30 minutes, (R)-2-bromo-4-methylpentanoic acid (10.1 g, 51.8 mmol) in DMF (20 mL) was added dropwise and the mixture was stirred at 0° C. to room temperature over 6 hours. The mixture was diluted with 100 mL EtOAc and extracted with 100 mL of a 1:1 1N HCl:saturated aqueous NaCl solution. The layers were separated and the aqueous phase was extracted with additional EtOAc (100 mL). The organics were combined, washed with saturated aqueous NaCl, dried over MgSO4, filtered, and concentrated under reduced pressure. The recovered oil was dissolved into diisopropyl ether (45 mL, 320 mmol) and chilled at 0° C. Dicyclohexylamine (10.1 mL, 50.7 mmol) was added dropwise and the solid was allowed to crash out of solution. After stirring for an additional 30 minutes the material was filtered and washed with 75 mL cold diisopropyl ether. The recovered solid (14 g) was suspended in 100 mL EtOAc. 150 mL of 5% $KHSO_4$ was added and the layers were separated. The organic was washed with saturated aqueous NaCl, dried over MgSO4, filtered, and concentrated under reduced pressure. The recovered oil was then azeotroped (3×25 mL toluene) to yield the title compound (6.1 g) as a dicyclohexylamine salt.

Preparation 5

Crystalline 4'-{5-[((S)-2-Acetylsulfanyl-4-methylpentanoylamino)methyl]-2-ethoxy-4-ethylimidazol-1-ylmethyl}-3'-fluorobiphenyl-2-carboxylic Acid

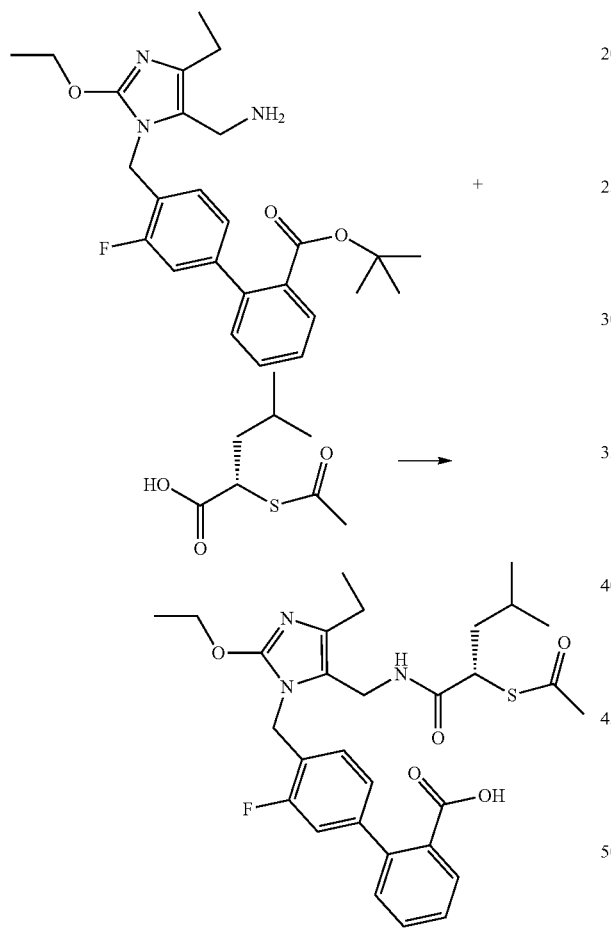

Crystalline 4'-(5-aminomethyl-2-ethoxy-4-ethylimidazol-1-ylmethyl)-3'-fluorobiphenyl-2-carboxylic acid t-butyl ester (dicyclohexylamine salt; 18 g, 40 mmol, 1 eq.), (S)-2-acetylsulfanyl-4-methylpentanoic acid (18 g, 48 mmol, 1.2 eq.), and HCTU (19 g, 48 mmol, 1.2 eq.) were combined in a pre-chilled vessel (0° C. for 10 minutes) and cold DCM (240 mL) was added. The mixture was stirred at 1±2° C. for 5-15 hours. 4% $NaHCO_3$ (200 mL) was added and the mixture was stirred for 15 minutes. The DCM layer was separated and distilled to ~100 mL. iPrOAc (150 mL) was added and distill to 150 mL. Additional iPrOAc (200 mL) was added and the mixture was washed with 4% $NaHCO_3$ (2×200 mL) and water (200 mL). The solution was stirred with 15% $NH_4Cl$ (300 mL) for 15 minutes, the pH was adjusted to 5.5 with 1N HCl, and then stirred for 1 hour. The solids were filtered off. The filtrate was washed with iPrOAc (50 mL), and the iPrOAc layer separated. The iPrOAc layer was stirred with 15% $NH_4Cl$ (200 mL) for 3 hours and any solids filtered off. The filtrate was washed with saturated aqueous NaCl (150 mL) and distilled under vacuum to ~60 mL. DCM (50 mL) was added and distilled off. DCM (200 mL) was added and the mixture was cooled 0-5° C. TFA (70 mL) was added slowly (slightly exothermic) at below 15° C., and the mixture was stirred at 20° C. for 16 hours. The mixture was concentrated to ~150 ml, and iPrOAc (150 mL) was added. The mixture was distilled to ~150 mL. Additional iPrOAc (150 mL) was added, and again distilled to ~150 mL. iPrOAc (200 mL) was added and the resulting solution was slowly added to pre-cooled $K_2CO_3$ (52 g) in water (250 mL) at below 10° C. (mildly exothermic, pH>7 must>6 during quench) over 15 minutes. The pH was monitored during the transfer, and additional base (8 g) was added when the pH dropped below 6. The iPrOAc layer was separated and washed with saturated aqueous NaCl (150 mL). The iPrOAc solution was distilled to ~50 mL. MTBE (100 mL) was added and the mixture distilled to ~50 mL. Additional MTBE (100 mL) was added and the mixture was stirred at room temperature for 3 hours, forming a slurry, which was then stirred at 4° C. for 16 hours. The solids were filtered off and washed with MTBE/diisopropyl ether (1:1; 100 mL). The solids were then dried at room temperature for 60 hours under nitrogen to yield the title compound as a crystalline material (18.2 g).

Example 1

Crystalline 4'-{2-Ethoxy-4-ethyl-5-[((S)-2-mercapto-4-methylpentanoylamino)methyl]imidazol-1-ylmethyl}-3'-fluorobiphenyl-2-carboxylic Acid

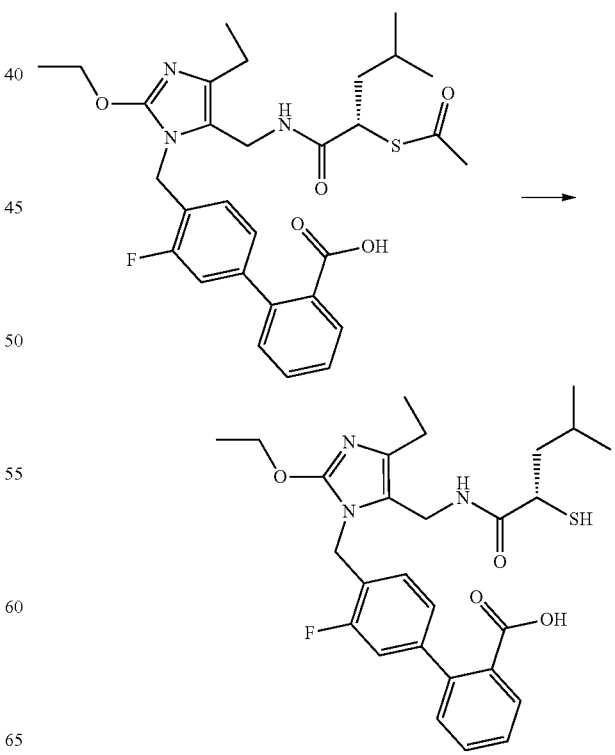

Crystalline 4'-{5-[((S)-2-acetylsulfanyl-4-methylpentanoylamino)methyl]-2-ethoxy-4-ethylimidazol-1-ylmethyl}-3'-fluorobiphenyl-2-carboxylic acid (2.3 g, 4 mmol, 1 eq.) and DTT (62 mg, 0.4 mmol, 0.1 eq.) was dissolved in MeOH (30 mL). The resulting solution was degassed with nitrogen (3 times) and cooled at 0° C. NaOMe (25% in MeOH, 1.7 mL) was added and the mixture was stirred at 0° C. for 30 minutes. AcOH (3 g, 50 mmol, 4 eq.) was added to quench the reaction at 0° C. The mixture was warmed to 20° C. Deionized water (10 mL) was added slowly. The mixture was stirred at 20° C. for 3 hours and then stirred at 4° C. for 1 hour until precipitates were formed. The solids were filtered and washed with MeOH/H$_2$O (2:1; 30 mL), then dried under nitrogen at 20° C. for 48 hours to yield the title crystalline compound (1.2 g).

Example 2

Micronization

Crystalline 4'-{2-ethoxy-4-ethyl-5-[((S)-2-mercapto-4-methylpentanoylamino)-methyl]imidazol-1-ylmethyl}-3'-fluorobiphenyl-2-carboxylic acid was micronized with a jet mill to give a free-flowing white powder. No issues were encountered during the micronization process. Particle size distribution was as follows:

|  | Pre-Micronization | Post-Micronization |
|---|---|---|
| D (v, 0.9) | 50.73 μm | 7.07 μm |
| D (v, 0.5) | 11.32 μm | 2.59 μm |
| D (v, 0.1) | 1.73 μm | 0.79 μm |

Example 3

Slurrying Procedure

Micronized crystalline 4'-{2-ethoxy-4-ethyl-5-[((S)-2-mercapto-4-methylpentanoylamino)methyl]imidazol-1-ylmethyl}-3'-fluorobiphenyl-2-carboxylic acid (500 mg, 0.9 mmol) was mixed with 20% acetone/water (7.5 mL) and stirred for 2½ hours at room temperature. The solids were filtered, washed with cold 10% acetone/water (3 mL). The filter cake was dried and the filtrate was lyophilized to yield 470 mg of the slurried micronized crystalline compound.

Example 4

Powder X-Ray Diffraction

Powder X-ray diffraction patterns were obtained with a Rigaku Miniflex PXRD diffractometer using CuKα (30.0 kV, 15.0 mA) radiation. The analysis was performed with the goniometer running in continuous-scan mode of 2° (2θ) per min with a step size of 0.03° over a range of 2 to 40° in two-theta angle. Samples were prepared on quartz specimen holders as a thin layer of powdered material. The instrument was calibrated with a silicon metal standard, within ±0.02° two-theta angle.

The PXRD pattern for a sample of the crystalline compound of Example 1 is shown in FIG. 1A. The PXRD pattern for a sample of the micronized crystalline compound of Example 2 is shown in FIG. 1B. The PXRD pattern for a sample of the slurried micronized crystalline compound of Example 3 is shown in FIG. 1C. No significant changes were observed in the PXRD pattern for the material of Example 2 compared to the material of Example 1. Similarly, no significant changes were observed in the PXRD pattern for the material of Example 3 compared to the material of Example 2.

Example 5

Thermal Analysis

Differential scanning calorimetry (DSC) was performed using a TA Instruments Model Q-100 module with a Thermal Analyst controller. Data were collected and analyzed using TA Instruments Thermal Solutions software. Samples of each material to be tested was accurately weighed into a covered aluminum pan. After a 5 minute isothermal equilibration period at 22° C., the samples were heated using a linear heating ramp of 10° C./min from 22° C. to 250° C. Three DSC runs were conducted for the crystalline compound of Example 1 and for the micronized crystalline compound of Example 2. One DSC run was conducted for the slurried micronized crystalline compound of Example 3. The following table presents the melting points of each of the three materials tested.

| Sample | DSC Run Peak Temperatures, ° C. | Average DSC Run Peak Temperature, ° C. |
|---|---|---|
| Ex. 1: crystal | 149.3, 149.6, 150.5 | 149.8 |
| Ex. 2: micronized crystal | 147.6, 147.8, 147.3 | 147.5 |
| Ex. 3: slurried micronized crystal | 149 | 149 |

Since DSC is a method used to study amorphous and crystalline materials, the results in this table, as well as the measured levels of impurities present over time, demonstrate that the slurrying process increases the stability of the micronized sample, as measured by peak temperature.

Example 6

Other Slurrying Inert Diluents

Micronized crystalline 4'-{2-ethoxy-4-ethyl-5-[((S)-2-mercapto-4-methylpentanoyl-amino)methyl]imidazol-1-ylmethyl}-3'-fluorobiphenyl-2-carboxylic acid was mixed with different inert diluents. Slurrying was done over times ranging from 1 to 5 hours and at temperatures ranging from 0° C. to 40° C.

| Inert diluent(s)s/duration/temperature | DSC |
|---|---|
| Ex. 1: crystal | 149.8 |
| Ex. 2: micronized crystal | 147.5, 147.2 |
| 10% MeCN/water, 1 hour, RT | 148.4 |
| 20% MeCN/water, 1 hour, RT | 149 |
| 30% MeCN/water, 1 hour, RT | 149.4 |
| 5% MeOH/water, 1 hour, RT | 149.2 |
| 10% MeOH/water, 1 hour, RT | 148.9 |
| 20% MeOH/water, 1 hour, RT | 148.5 |
| 30% MeOH/water, 1 hour, RT | 149 |
| 5% IPA/water, 1 hour, RT | 149 |
| 10% IPA/water, 1 hour, RT | 149.1 |
| 20% IPA/water, 1 hour, RT | 149 |
| 30% IPA/water, 1 hour, RT | 149 |
| 5% Acetone/water, 1 hour, RT | 149 |
| 10% Acetone/water, 1 hour, RT | 149.2 |
| 20% Acetone/water, 1 hour, 0° C. | 149.2 |

-continued

| Inert diluent(s)s/duration/temperature | DSC |
|---|---|
| 20% Acetone/water, 1 hour, RT | 149.3 |
| 20% Acetone/water, 1 hour, 40° C. | 149.4 |
| 20% Acetone/water, 5 hours, 0° C. | 149 |
| 20% Acetone/water, 5 hours, RT | 149.1 |
| 20% Acetone/water, 5 hours, 40° C. | 149.5 |
| 30% Acetone/water, 1 hour, RT | 149.4 |
| Toluene, 4 hours, 0° C. | 147.7 |
| Toluene, 4 hours, RT | 147.7 |
| Toluene, 1.5 hours, 40° C. | 148.2 |
| iPrOAc, 4 hours, 0° C. | 149.1 |
| iPrOAc, 4 hours, RT | 149 |
| iPrOAc, 1.5 hours, 40° C. | 149.6 |
| MTBE, 4 hours, 0° C. | 148.2 |
| MTBE, 4 hours, RT | 148.3 |
| MTBE, 1.5 hours, 40° C. | 148.8 |

RT = room temperature

The results in this table demonstrate that several other inert diluents and slurrying conditions can be used in the process of the invention, in order to elevate the peak temperature of the micronized sample.

Example 7

Solid State Stability Assessment

Samples of the crystalline 4'-{2-ethoxy-4-ethyl-5-[((S)-2-mercapto-4-methylpentanoyl-amino)methyl]imidazol-1-ylmethyl}-3'-fluorobiphenyl-2-carboxylic acid, the micronized crystalline compound, and the slurried micronized crystalline compound, about 15 mg each, were stored in multiple closed vials at 40° C. (with 1 g Molecular Sieve 4A dessicant included). At specific intervals, the entire contents of representative vials were analyzed by the following HPLC method:

Column: Agilent Zorbox SB-C18, 4.6×250 mm, 5 μm (Part No. 880975-902). Mobile Phase A: 80% water, 20% MeCN, 0.01% TFA. Mobile Phase B: 20% water, 80% MeCN, 0.01% TFA. Flow rate: 1 mL/min. Injection Volume: 20 μL. Detector: 225 nm.

Samples were prepared as 0.2-0.3 mg/mL stock solutions in 40% MeOH and 60% MeCN in water, depending on the solubility, for injection onto the HPLC. The amount of 4'-{2-ethoxy-4-ethyl-5-[(2-mercapto-4-methylpentanoylamino)methyl]imidazol-1-ylmethyl}-3'-fluorobiphenyl-2-carboxylic acid ethyl ester (M+28) and 4'-{4-ethyl-5-[(2-mercapto-4-methylpentanoylamino)methyl]-2-oxo-2,3-dihydroimidazol-1-ylmethyl}-3'-fluorobiphenyl-2-carboxylic acid (M−28) present were determined by HPLC area percentage (% AUC or area/area %).

| Material | T = 0 % M + 28 | 2 weeks % M + 28 | 2 weeks Δ % M + 28 | 4 weeks % M + 28 | 4 weeks Δ % M + 28 |
|---|---|---|---|---|---|
| Ex. 1: crystal | 0 | 0.05 | 0.05 | 0.05 | 0.05 |
| Ex. 2: micronized crystal | 0.10 | 0.40 | 0.30 | 0.44 | 0.34 |
| Ex. 3: slurried micronized crystal | 0.06 | 0.07 | 0.01 | 0.08 | 0.02 |

| Material | T = 0 % M − 28 | 2 weeks % M − 28 | 2 weeks Δ % M − 28 | 4 weeks % M − 28 | 4 weeks Δ % M − 28 |
|---|---|---|---|---|---|
| Ex. 1: crystal | 0.05 | 0.04 | −0.01 | 0.05 | 0 |
| Ex. 2: micronized crystal | 0.09 | 0.47 | 0.38 | 0.61 | 0.52 |
| Ex. 3: slurried micronized crystal | 0.15 | 0.20 | 0.05 | 0.24 | 0.09 |

The results in this table demonstrate that the stability of the micronized sample increases significantly after the slurrying.

After being maintained at a temperature of about 40° C. for at least 2 weeks, the M+28 present in the micronized crystalline compound of Example 2 increased by about 0.30% (relative to the amount of M+28 at time zero), and the M−28 present in this micronized crystalline compound increased by about 0.38% (relative to the amount of M−28 at time zero). Thus, a significant increase in the amount of both impurities is observed in the micronized material.

Under the same storage conditions, the M+28 present in the slurried micronized crystalline compound of Example 3 only increased by about 0.01%, relative to the amount of M+28 at time zero. Even after storage for 4 weeks, the M+28 present in the slurried micronized crystalline compound of Example 3 only increased by about 0.02%, relative to the amount of M+28 at time zero.

Under the same storage conditions, the M−28 present in the slurried micronized crystalline compound of Example 3 only increased by about 0.05%, relative to the amount of M−28 at time zero. Even after storage for 4 weeks, the M−28 present in the slurried micronized crystalline compound of Example 3 only increased by about 0.09%, relative to the amount of M−28 at time zero.

Thus, the stable micronized acid imidazole of the invention exhibits a minimal increase in the amount of impurities compared to that observed with the micronized material. The amounts of both the M+28 and the M−28 do not increase by more than about 0.1% AUC by HPLC relative to the initial amount of acid imidazole, when maintained at a temperature of about 40° C. for at least 2 weeks as well as when maintained at a temperature of about 40° C. for at least 4 weeks.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. Stable micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid, characterized by a powder x-ray diffraction pattern comprising diffraction peaks at 2Θ values of 6.66±0.20, 9.8±0.20, and 18.12±0.20, where the amount of 4'-{2-ethoxy-4-ethyl-5-[(2-mercapto-4-methylpentanoylamino)methyl]imidazol-1-ylmethyl}-3'-fluorobiphenyl-2-carboxylic acid ethyl ester within the stable micronized acid imidazole does not increase by more than about 0.1% AUC by HPLC relative to the initial amount of acid imidazole, when the stable micronized acid imidazole is maintained at a temperature of about 40° C. for at least 2 weeks.

2. The compound of claim 1, characterized by having one or more additional diffraction peaks at 2θ values selected from 12.68±0.20, 13.54±0.20, 15.02±0.20, 19.32±0.20, 21.20±0.20, 22.62±0.20, 24.56±0.20, 25.30±0.20, 25.96±0.20, and 27.32±0.20.

3. The compound of claim 1, characterized by a powder x-ray diffraction pattern in which the peak positions are substantially in accordance with the peak positions of the pattern shown in FIG. 1C.

4. The compound of claim 1, characterized by a DSC thermogram having an endotherm with a peak temperature of at least about 149° C.

5. A process for preparing the compound of claim 1 comprising: a) micronizing a sample of 4'-{2-ethoxy-4-ethyl-5-[((S)-2-mercapto-4-methylpentanoylamino)methyl]imidazol-1-ylmethyl}-3'-fluorobiphenyl-2-carboxylic acid; b) forming a slurry with the sample and an inert diluent for about 1 to about 10 hours; c) recovering stable micronized 4'-{2-ethoxy-4-ethyl-5-[((S)-2-mercapto-4-methylpentanoylamino)methyl]imidazol-1-ylmethyl}-3'-fluorobiphenyl-2-carboxylic acid, where the amount of 4'-{2-ethoxy-4-ethyl-5-[(2-mercapto-4-methylpentanoylamino)methyl]imidazol-1-ylmethyl}-3'-fluorobiphenyl-2-carboxylic acid ethyl ester within the stable micronized acid imidazole does not increase by more than about 0.1% AUC by HPLC relative to the initial amount of acid imidazole, when the stable micronized acid imidazole is maintained at a temperature of about 40° C. for at least 2 weeks.

6. The process of claim 5, wherein the inert diluent is selected from isopropyl acetate, methyl t-butyl ether, toluene, acetone with water, acetonitrile with water, methanol and water, and isopropanol and water.

7. The process of claim 6, wherein the inert diluent is acetone and water.

8. The process of claim 7, where the volume ratio of acetone to water is about 5:95 to 40:60.

9. The process of claim 8, where the volume ratio of acetone to water is about 10:90 to 30:70.

10. The process of claim 5, wherein the slurrying step is conducted at a temperature in the range of from about 0° C. to about 50° C.

11. The process of claim 10, wherein the temperature is about room temperature.

12. The process of claim 5, wherein the slurrying step is conducted for about 1 to about 10 hours.

13. The process of claim 12, wherein the slurrying step is conducted for about 1 to about 5 hours.

14. The product prepared by the process of claim 5.

15. A solid pharmaceutical composition comprising the compound of claim 1 and a pharmaceutically acceptable carrier.

16. A method of treating hypertension or heart failure, comprising administering a therapeutically effective amount of the compound of claim 1 to a patient in need thereof.

\* \* \* \* \*